United States Patent
Harper et al.

(10) Patent No.: US 6,464,688 B1
(45) Date of Patent: Oct. 15, 2002

(54) OSMOTIC PUMP DELIVERY SYSTEM WITH FLEXIBLE DRUG COMPARTMENT

(75) Inventors: Derek J. Harper, Santa Barbara, CA (US); Charles F. Milo, Atherton, CA (US)

(73) Assignee: Microsolutions, Inc., Santa Barbara, CA (US)

( * ) Notice: Subject to any disclaimer, the term of this patent is extended or adjusted under 35 U.S.C. 154(b) by 0 days.

(21) Appl. No.: 09/504,971

(22) Filed: Feb. 15, 2000

(51) Int. Cl.[7] ............................................. A61M 31/00
(52) U.S. Cl. ................................. 604/892.1; 604/891.1
(58) Field of Search ........................ 604/890.1, 891.1, 604/892.1; 424/422, 424

(56) References Cited

U.S. PATENT DOCUMENTS

| | | | |
|---|---|---|---|
| 3,760,805 A | * 9/1973 | Higuchi | 604/892.1 |
| 3,760,984 A | 9/1973 | Theeuwes | |
| 3,845,770 A | 11/1974 | Theeuwes | |
| 3,916,899 A | 11/1975 | Theeuwes | |
| 3,977,404 A | 8/1976 | Theeuwes | |
| 4,008,719 A | 2/1977 | Theeuwes et al. | |
| 4,014,334 A | 3/1977 | Theeuwes | |
| 4,034,758 A | 7/1977 | Theeuwes | |
| 4,036,227 A | 7/1977 | Zaffaroni et al. | |
| 4,036,228 A | 7/1977 | Theeuwes | |
| 4,058,122 A | 11/1977 | Theeuwes et al. | |
| 4,077,407 A | 3/1978 | Theeuwes et al. | |
| 4,093,708 A | 6/1978 | Zaffaroni et al. | |
| 4,096,238 A | 6/1978 | Zaffaroni et al. | |
| 4,111,201 A | 9/1978 | Theeuwes | |
| 4,111,202 A | 9/1978 | Theeuwes | |

(List continued on next page.)

FOREIGN PATENT DOCUMENTS

| | | | |
|---|---|---|---|
| JP | 05168639 A | * 7/1993 | 604/890.1 |
| WO | WO 00/54745 | 3/1999 | |

OTHER PUBLICATIONS

F. Theewes et al, *Principles Of The Design And Operation Of Generic OsmoticPpumps For The Delivery Of Semisolid Or Liquid Drug Formulations*, Annals Of Biomedical Engineering, 4, pp. 343–353, 1976.

F.P. Boersma, M.D.; H. Noorduin, M.SC. and G. Vanden Bussche, M.D., *Epidural Sufentanil For Cancer Pain Control In Outpatients*, Regional Anesthesia, Nov.–Dec. vol. 14, No. 6, pp. 293–297, 1989.

(List continued on next page.)

Primary Examiner—J. Casimer Jacyna
(74) Attorney, Agent, or Firm—Young Law Firm, P.C.

(57) ABSTRACT

An implantable osmotic pump system includes a rigid pump housing defining an opening adapted to receive a catheter; one or more membrane assemblies fitted to the pump housing; an osmotic engine within the rigid pump housing and a flexible pharmaceutical agent compartment disposed within the pump housing. The flexible pharmaceutical agent compartment is adapted to enclose a volume of a pharmaceutical agent and to cause the pharmaceutical agent to be infused through the opening as water crosses the membrane assembly or assemblies and increases the volume of the osmotic engine. The flexible pharmaceutical agent compartment may include polyethylene teraphthalate (PET), for example, and/or may include a metallic layer such as gold, silver, platinum and/or aluminum, for example, to inhibit the transfer of gas or liquid across the compartment. A catheter may be bonded to the opening of the pump housing and to a corresponding opening in the flexible pharmaceutical agent compartment. The flexible pharmaceutical agent compartment may be free floating inside the pump housing, being only attached to the catheter and/or to the opening of the pump housing. As the present implantable osmotic pump does not include a movable piston, the pump housing may have a cylindrical shape in which the height of the pump housing is less than the diameter thereof, a non-cylindrical shape and/or a shape that conforms to the patient's anatomy at the implant site.

45 Claims, 2 Drawing Sheets

U.S. PATENT DOCUMENTS

| | | | |
|---|---|---|---|
| 4,111,203 A | 9/1978 | Theeuwes | |
| 4,116,241 A | 9/1978 | Theeuwes | |
| 4,135,514 A | 1/1979 | Zaffaroni et al. | |
| 4,142,526 A | 3/1979 | Zaffaroni et al. | |
| 4,160,020 A | 7/1979 | Ayer et al. | |
| 4,160,452 A | 7/1979 | Theeuwes | |
| 4,193,398 A | 3/1980 | Refson | |
| 4,200,098 A | 4/1980 | Ayer et al. | |
| 4,203,439 A | 5/1980 | Theeuwes | |
| 4,256,108 A | 3/1981 | Theeuwes | |
| 4,265,874 A | 5/1981 | Bonsen et al. | |
| 4,278,087 A | 7/1981 | Theeuwes | |
| 4,285,987 A | 8/1981 | Ayer et al. | |
| 4,298,003 A | 11/1981 | Theeuwes et al. | |
| 4,327,725 A | 5/1982 | Cortese et al. | |
| 4,331,728 A | 5/1982 | Theeuwes | |
| 4,344,929 A | 8/1982 | Bonsen et al. | |
| 4,410,328 A | 10/1983 | Theeuwes | 604/892.1 |
| 4,449,983 A | 5/1984 | Cortese et al. | |
| 4,455,143 A | 6/1984 | Theewes et al. | |
| 4,455,145 A | 6/1984 | Theeuwes | 604/892.1 |
| 4,503,030 A | 3/1985 | Edgren et al. | |
| 4,552,561 A | 11/1985 | Eckenhoff et al. | 604/891.1 |
| 4,576,604 A | 3/1986 | Guittard et al. | |
| 4,578,075 A | 3/1986 | Urquhart et al. | |
| 4,587,117 A | 5/1986 | Edgren | |
| 4,608,048 A | 8/1986 | Cortese et al. | 604/892.1 |
| 4,610,686 A | 9/1986 | Ayer et al. | |
| 4,612,008 A | 9/1986 | Wong et al. | |
| 4,615,698 A | 10/1986 | Guittard et al. | |
| 4,619,652 A | 10/1986 | Eckenhoff et al. | |
| 4,627,850 A | 12/1986 | Deters et al. | |
| 4,627,851 A | 12/1986 | Wong et al. | |
| 4,655,766 A | 4/1987 | Theeuwes et al. | |
| 4,673,405 A | 6/1987 | Guittard et al. | |
| 4,685,918 A | 8/1987 | Amidon et al. | |
| 4,705,515 A | 11/1987 | Wong et al. | |
| 4,711,251 A | 12/1987 | Stokes | |
| 4,723,958 A | 2/1988 | Pope | |
| 4,732,915 A | 3/1988 | Ayer et al. | |
| 4,751,071 A | 6/1988 | Magruder et al. | |
| 4,756,314 A | 7/1988 | Eckenhoff et al. | |
| 4,765,989 A | 8/1988 | Wong et al. | |
| 4,777,049 A | 10/1988 | Magruder et al. | |
| 4,783,337 A | 11/1988 | Wong et al. | |
| 4,783,413 A | 11/1988 | Suter | |
| 4,837,111 A | 6/1989 | Deters et al. | |
| 4,851,228 A | 7/1989 | Zentner | |
| 4,851,229 A | 7/1989 | Magruder et al. | |
| 4,880,631 A | 11/1989 | Haslam et al. | |
| 4,886,668 A | 12/1989 | Haslam et al. | |
| 4,898,582 A | 2/1990 | Faste | |
| 4,968,507 A | 11/1990 | Zentner | |
| 4,976,966 A | 12/1990 | Theeuwes et al. | |
| 5,030,216 A | 7/1991 | Theewes et al. | |
| 5,151,093 A | 9/1992 | Theewes et al. | |
| 5,169,390 A | 12/1992 | Athayde et al. | |
| 5,257,987 A | 11/1993 | Athayde et al. | 604/892.1 |
| 5,273,752 A | 12/1993 | Ayer et al. | |
| 5,279,608 A | 1/1994 | Cherif Cheikh | |
| 5,312,389 A | 5/1994 | Theeuwes et al. | |
| 5,318,540 A | 6/1994 | Athayde et al. | |
| 5,324,280 A | 6/1994 | Wong et al. | |
| 5,413,572 A | 5/1995 | Wong et al. | |
| 5,492,534 A | 2/1996 | Athayde et al. | |
| 5,562,654 A | 10/1996 | Smith | |
| 5,612,059 A | 3/1997 | Cardinal et al. | |
| 5,672,167 A | 9/1997 | Athayde et al. | |
| 5,698,220 A | 12/1997 | Cardinal et al. | |
| 5,728,396 A | 3/1998 | Peery et al. | |
| 5,795,591 A | 8/1998 | Lee et al. | |
| 5,798,119 A | 8/1998 | Herbig et al. | |
| 5,801,188 A | 9/1998 | Hassenbusch | |
| 5,827,538 A | 10/1998 | Cussler et al. | |
| 5,869,096 A | 2/1999 | Barclay | |
| 5,869,097 A | 2/1999 | Wong | |
| 5,876,752 A | 3/1999 | Herbig | |
| 5,904,934 A | 5/1999 | Maruyama | |
| 5,980,509 A | 11/1999 | Magruder | |
| 5,985,305 A | 11/1999 | Peery | |
| 5,997,527 A | 12/1999 | Gumucio et al. | |

OTHER PUBLICATIONS

Tim J. Lamer, M.D.; Symposium on Pain Management–Part II, *Treatment Of Cancer–Related Pain: When Orally Administered Medications Fail*, Mayo Clinic Proc., 69, pp. 473–480, 1994.

T.F. Meert and M. DeKock, *Potentiation Of The Analgesic Properties Of Fentanyl–Like Opioids With Alpha2–Adrenoceptor Agonists In Rats*, Anesthesiology, Sep., 81(3), pp. 677–688, 1994.

A. Paix, A. Coleman, J. Lees, J. Grigson, M. Brooksbank, D. Thorne and M. Ashby, *Subcutaneous Fentanyl And Sufentanil Infusion Substitution For Morphine Intolerance In Cancer Pain Management*, Pain, Nov.; 63(2), pp. 263–269, 1995.

F. Mercier, M. Dounas, H. Bouaziz, V. Des Mesnard–Smaja, C. Foiret, M.N. Vestermann, M. Fischler and D. Benhamou, *The Effect Of Adding A Minidose Of Clonidine To Intrathecal Sufentanil For Labor Analgesia*, Anesthesiology, Sep. 89(3), pp. 594–601, 1998.

Alzet Osmotic Pumps, *References from 1991–1998 On The Administration Of Opiods Using ALZET Osmotic Pumps (OPIO–Q4–99)*, pp. 1–13, World Wide Web, http://www.alzet.com/bibliography/bib_pages/opio.htm (Printed on Oct. 13, 2000.

F. Theeuwes et al, *Principles of the design and operation of generic osmotic pumps for the delivery of semisolid or liquid drug formulations*, Annals of Biomedical Engineering 4, 343–353 (1976).

Edith Mathiowitz; (Ed.), *Encyclopedia of Controlled Drug Delivery*, vol. 2, 1999 John Wiley & Sons, ISBN 047116634, p896–920.

Tony Yaksh (Ed.), *Spinal Drug Delivery, Chapter 13, Animal Models of intrathecal and epidural drug delivery*, p317–344, 1999 Elsevier Science, ISBN 0444829016.

Tony Yaksh (Ed.), *Spinal Drug Delivery, Chapter 14, Human spinal drug delivery: methods and technology*, Mark Wallace, p345–370, 1999 Elsevier Science, ISBN 0444829016.

* cited by examiner

OSMOTIC PUMP DELIVERY SYSTEM WITH FLEXIBLE DRUG COMPARTMENT

CROSS-REFERENCE TO RELATED APPLICATIONS

This application is related in subject matter to commonly assigned co-pending patent application Ser. No. 09/442,128 filed on Nov. 16, 1999 entitled "Methods And Implantable Devices And Systems For Long Term Delivery Of A Pharmaceutical Agent", the disclosure of which is hereby incorporated herein in its entirety.

This application is also related in subject matter to commonly assigned co-pending patent application Ser. No. 09/503,821 filed on Feb. 15, 2000 and entitled "Osmotic Pump Drug Delivery Systems And Methods", the disclosure of which is also hereby incorporated herein in its entirety.

This application is also related in subject matter to commonly assigned co-pending patent application Ser. No. 09/504,603 filed on Feb. 15, 2000 and entitled "Osmotic Pump Delivery System With Pre-Hydrated Membranes(s) And/Or Primable Catheter", the disclosure of which is also hereby incorporated herein in its entirety.

BACKGROUND OF THE INVENTION

1. Field of the Invention

The present invention relates generally to the field of drug delivery systems. In particular, the present invention relates to osmotic pump systems.

2. Description of the Related Art

Since the beginning of modern medicine, drugs have been administered orally. Patients have taken pills as recommended by their physician. The pills must pass through the digestive system and then the liver before they reach their intended delivery site (e.g., the vascular system). The actions of the digestive tract and the liver often reduce the efficacy of medication; furthermore, medications delivered systemically sometimes cause undesirable side effects. Over the course of the past few decades, drug delivery technology and administration has evolved from oral delivery to site-specific delivery. In addition to the oral route of administration, drugs are also routinely administered via the vascular system (intravenous or IV). Intravenous drug delivery has the advantage of bypassing the acidic and enzymatic action of the digestive system. Unfortunately, IV administration requires the use of a percutaneous catheter or needle to deliver the drug to the vein. The percutaneous site requires extra cleanliness and maintenance to minimize the risk of infection. Infection is such a significant risk that IV administration is often limited to a number of weeks, at most. In addition, the patient must wear an external pump connected to the percutaneous catheter.

The next step in the evolution of drug delivery was the implanted pump. The implanted pump is a device that is completely implanted under the skin of a patient, thereby negating the need for a percutaneous catheter. These implanted pumps provide the patient with a drug at a constant or a programmed delivery rate. Constant rate or programmable rate pumps are based on either phase-change or peristaltic technology. When a constant, unchanging delivery rate is required, a constant-rate pump is well suited for long-term implanted drug delivery. If changes to the infusion rate are expected, a programmable pump may be used in place of the constant rate pump. Fully implanted constant rate and programmable rate infusion pumps have been sold in the United States for human use since the late 1970s and early 1980s, respectively. Two problems associated with such 1970s and 1980s vintage constant rate and programmable rate infusion pumps relate to their size and their cost. Current implantable constant rate and programmable pumps are about the size and shape of hockey pucks, and they typically are sold to the hospital for $5,000–$9,000. The current implantable pumps must be implanted in the Operating Room under general anesthesia, which further increases costs, as well as the risk, and discomfort to the patient. The size and cost of such pumps has proven to be a substantial barrier to their use, and they are rarely used to deliver medication. An added drawback of phase-change and peristaltic pumps is that they must be refilled with drug every 3–8 weeks. Refills constitute an added burden to the caregiver, and add further costs to an already overburdened healthcare system. The burden associated with such refills, therefore, further limits the use of phase-change and peristaltic pumps.

In the 1970s, a new approach toward implanted pump design was commercialized for animal use only. The driving force of the pumps based upon this new approach utilized the principle of osmosis. Osmotic pumps may be much smaller than other constant rate or programmable pumps, because their infusion rate can be very low. A recent example of such a pump is described listed in U.S. Pat. No. 5,728,396. This patent discloses an implantable osmotic pump that achieves a sustained delivery of leuprolide. The pump includes a cylindrical impermeable reservoir that is divided into a water-swellable agent chamber and a drug chamber, the two chambers being divided by a movable piston. Fluid from the body is imbibed through a semi permeable membrane into the water-swellable agent chamber. As the water-swellable agent in the water-swellable agent chamber expands in volume, it pushes on the movable piston, which correspondingly decreases the volume of the drug chamber and causes the drug to be released through a diffusion outlet at a substantially constant rate.

The aspect ratio of such cylindrical osmotic pump delivery devices is large, and often not compatible with the human body. Indeed, the human body does not have naturally-formed cylindrical cavities in which to implant such devices in the patient, in an unobtrusive and comfortable manner. The principal reason for the cylindrical designs of conventional osmotic pump drug delivery systems is that they rely upon a movable piston design to push out a volume of drug from the drug chamber as the osmotic water-swellable agent expands. Pistons, however, must be cylindrical to avoid binding the pump housing as the piston moves. This problem is exacerbated by the fact that the water-swellable agent within the water-swellable agent compartment often does not expand evenly, which may exert localized increased pressure on the piston, causing the piston to bind within the pump housing. In turn, this binding may affect the delivery rate of the device and reduce the therapeutic benefits of the implantable pump.

What are needed, therefore, are non-cylindrical implantable osmotic pumps. What are also needed are implantable osmotic pumps that conform to the patient's anatomy and that more closely match the topology of the implant site. Also needed are novel implantable osmotic pump designs that do not rely upon a piston to infuse a drug or drugs into the patient.

SUMMARY OF THE INVENTION

It is an object of the present invention, therefore, to provide non-cylindrical implantable osmotic pumps. It is also an object of the present invention to provide implantable osmotic pumps that conform to the patient's anatomy and that more closely match the topology of the implant site. Another object of the present invention is to provide novel implantable osmotic pump designs that do not rely upon a piston to infuse a drug or drugs into the patient.

In accordance with the above-described objects and those that will be mentioned and will become apparent below, an implantable osmotic pump system, according to an embodiment of the present invention, includes a rigid pump housing defining an opening; at least one membrane assembly fitted to the pump housing; an osmotic engine within the rigid pump housing, and a flexible pharmaceutical agent compartment disposed within the rigid pump housing, the flexible pharmaceutical agent compartment being in fluid communication with the opening.

According to further embodiments, the membrane assembly may include a semipermeable membrane and may include an impermeable membrane initially sealing the semipermeable membrane, the impermeable membrane being adapted to be breached by a lancet. The impermeable membrane may be disposed away from the semipermeable membrane to define a fluid tight compartment therewith, which compartment may enclose a volume of saturated saline solution. The impermeable membrane may include a biologically inert material that is impermeable to water and that may be radiopaque. The impermeable membrane may include titanium, steel, polyethylene, polyethylene teraphthalate (PET), PETG and/or PETE. The impermeable membrane may include or be coated with a layer of gold, silver, platinum and/or platinum-iridium, for example.

The osmotic engine may include a "conventional" osmotic engine. Instead of a "salt block", the osmotic engine may include a "salt wafer". The osmotic engine may be a hygroscopic salt and/or may include an absorbent polymer. The absorbent polymer may include a material selected from a group including poly(acrylic acid), potassium salt; poly (acrylic acid), sodium salt; poly(acrylic acid-co-acrylamide), potassium salt; poly(acrylic acid), sodium salt-graft-poly(ethylene oxide); poly (2-hydroxyethyl methacrylate); poly(2-hydroxypropyl methacrylate) and poly(isobutylene-co-maleic acid) or derivatives thereof.

The pharmaceutical agent may be therapeutically effective for pain therapy, hormone therapy, gene therapy, angiogenic therapy, anti-tumor therapy, chemotherapy and/or other pharmaceutical therapies. For example, the pharmaceutical agent may include an opioid. The pharmaceutical agent may include an agonist, a partial agonist, an agonist-antagonist and/or an alpha 2-adrenoreceptor agonist, for example. According to further embodiments, the pharmaceutical agent may include one or more of the following drugs: morphine, hydromorphone, levorphanol, methadone, fentanyl, sufentanil, buprenorphine, pentazocine, butorphanol or the like.

The flexible pharmaceutical agent compartment may be made of or include a substantially impermeable material and may include polyethylene, PET, PETG and/or PETE and may be laminated with gold, silver, platinum, aluminum or other metal(s) to increase impermeability to gases and liquids. A catheter may be bonded to the opening of the pump housing and to a corresponding opening in the flexible pharmaceutical agent compartment so as to define a fluid path from the flexible pharmaceutical agent compartment through the opening of the pump housing to the catheter. According to one embodiment, the flexible pharmaceutical agent compartment may be free floating inside the pump housing and may be attached only to the catheter and/or the opening of the pump housing. The pump housing may have a non-cylindrical shape and/or may have a shape that conforms to a patient anatomy at an implantation site.

The pump housing may include a proximal end, a distal end and a sidewall, and one or more membrane assemblies may be fitted to the sidewall. The membrane assembly or assemblies may include an array of membrane assemblies, each of which may include a semipermeable membrane initially sealed by a radiopaque impermeable membrane adapted to be breached with a lancet.

The present invention is also an implantable osmotic pump, comprising a pump housing; an osmotic engine, the osmotic engine being disposed within the pump housing; a semipermeable membrane, the semipermeable membrane being configured to allow water to cross from a patient into the pump housing to the osmotic engine, and a flexible pharmaceutical agent compartment adapted to enclose a volume of pharmaceutical agent.

The flexible pharmaceutical agent compartment may be adapted to infuse the volume of pharmaceutical agent at a selected infusion rate as the osmotic engine hydrates and swells with the water from the patient, the selected infusion rate being related to the thickness, the composition and/or the surface area of the semipermeable membrane or to the sum of the individual contributions of the thickness, composition and surface area of the semipermeable membrane. The pump housing may include a proximal end, a distal end and a sidewall, and the semipermeable membrane may be fitted to the sidewall. The pump housing may include a proximal end, a distal end and a sidewall, and the semipermeable membrane may be fitted to the proximal end. A plurality of semipermeable membranes may be provided, each being adapted to allow water to cross into the osmotic engine. Each of the plurality of semipermeable membranes may be fitted with an impermeable membrane that initially seals the semipermeable membrane. The impermeable membrane may radiopaque. The osmotic engine may be at least co-extensive with the flexible pharmaceutical agent compartment. The pump housing may be cylindrical or may have a non-cylindrical shape.

The pharmaceutical agent may be therapeutically effective for pain therapy, hormone therapy, gene therapy, angiogenic therapy, anti-tumor therapy, chemotherapy and/or other pharmaceutical therapies. The pharmaceutical agent may include an opioid and/or may include an agonist, a partial agonist, an agonist-antagonist and/or an alpha 2-adrenoreceptor agonist. For example, the pharmaceutical agent may include one or more of the following drugs: morphine, hydromorphone, levorphanol, methadone, fentanyl, sufentanil, buprenorphine, pentazocine, butorphanol or the like.

BRIEF DESCRIPTION OF THE DRAWINGS

For a further understanding of the objects and advantages of the present invention, reference should be made to the following detailed description, taken in conjunction with the accompanying figures, in which:

FIG. 4b shows a top view of the membrane assembly of FIG. 4a.

DESCRIPTION OF THE INVENTION

Figure 1:
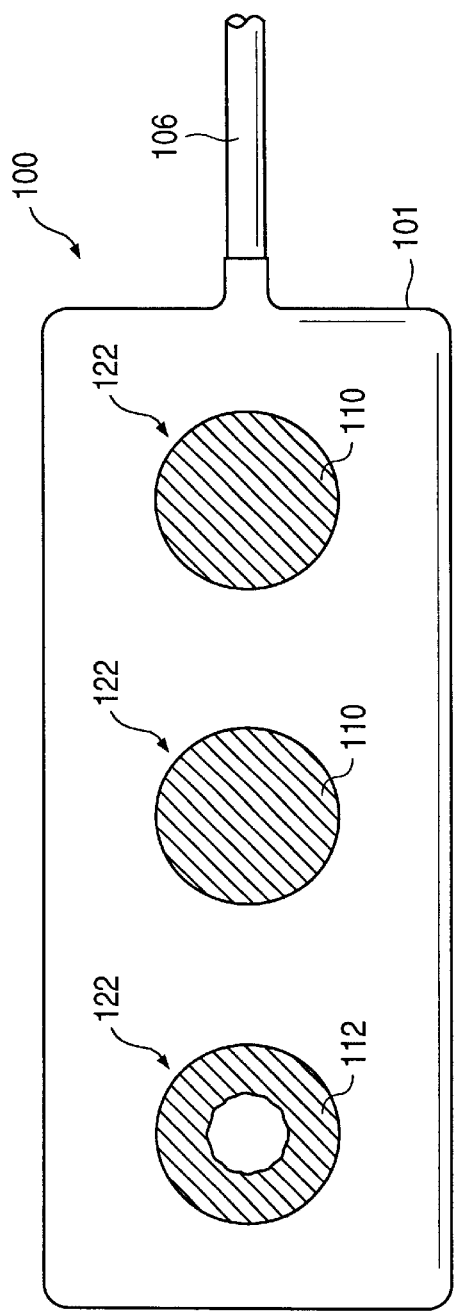
FIG. 1 shows a top view of an implantable osmotic pump according to an embodiment of the present invention.

FIG. 1 shows a top view of a implantable system 100 for the delivery of a pharmaceutical agent to a patient, according to an embodiment of the present invention. The system 100 includes a pump housing 101 and a catheter 106. The pump housing 101 is fitted with a least one membrane assembly 122. The pump housing 101 may be substantially rectangular in shape, cylindrical or most any shape, including non-symmetrical irregular shapes. In the embodiment shown in FIGS. 1, 2 and 3, the pump housing 101 includes three such membrane assemblies 122, linearly arranged. To accommodate such membrane assemblies 122, the pump housing 101 may include a substantially flat portion. Alternatively, the membrane assemblies may be fitted to the radius of curvature of the pump housing 101.

Figure 2:
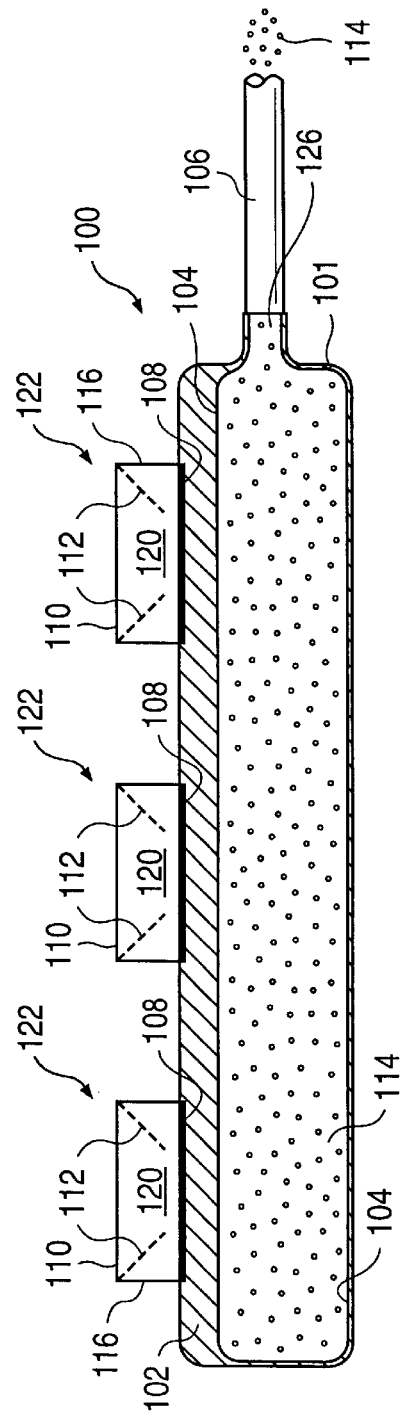
FIG. 2 shows a side cross-sectional view of the implantable osmotic pump of FIG. 1, showing the flexible pharmaceutical agent compartment in its original, filled state.

FIG. 2 is a cross-sectional side view of the delivery system 100. As shown therein, the membrane assemblies 122 each may include a semipermeable membrane 108. The semipermeable membrane 108 may include a hygroscopic material, including polyurethane, polyamide, an elastomeric composition and/or a cellulose acetate composition, for example. The semipermeable membranes 108 allow water from the patient (not shown) to reach the interior of the pump housing 101. The membrane assemblies 122 may each further include a water impermeable membrane 110. The impermeable membrane 110 may include or be formed of most any water impermeable material that is biologically inert, such as titanium and/or stainless steel, coated platinum or platinum-iridium for radiopacity, for example. Alternatively, the impermeable membrane 110 may include polyethylene, PET, PETG or PETE, for example. Preferably, the impermeable membrane 110 is radiopaque, so as to be visible under fluoroscopy, once implanted. For example, a layer of radiopaque material may be sputtered or otherwise deposited on the impermeable membrane 110, to render it visible under fluoroscopy. Preferably, the impermeable membranes 110 are adapted to be breached by the physician or clinician, using a lancet (such as shown at 118 in FIGS. 4a and 5a), or some other functionally similar device. The impermeable membrane 110 initially seals the semipermeable membrane 108, to prevent any water originating from the patient's implant site from crossing the semipermeable membrane 108 until the impermeable membrane(s) 110 is breached, as shown in dashed lines at reference numeral 112 in FIG. 2. The impermeable membrane 110 may be disposed away from the semipermeable membrane 108 and supported by a cylindrical (for example) spacer 116 so as to define a fluid tight compartment 120 therewith. To maintain an osmotic equipotential across the semipermeable membrane 108 and to maintain the semipermeable membrane 108 in a fully hydrated state, the fluid tight compartment 120 may contain a saturated saline solution 124, as disclosed in the above-identified co-pending and commonly assigned US patent application entitled "Osmotic Pump Delivery System With Pre-Hydrated Membrane(S) And/Or Primable Catheter".

As further shown in FIG. 2, the rigid pump housing 101 according to the present invention includes a flexible pharmaceutical agent compartment 104 and an osmotic engine 102. The flexible pharmaceutical agent compartment 104 may, as shown in FIG. 2, enclose a volume of a pharmaceutical agent 114. As water from the patient implant site crosses the semipermeable membrane(s) 108 of the membrane assembly or assemblies 122, the osmotic engine 102 hydrates and swells (increases in volume). As the osmotic engine 102 increases in volume, it pushes against and correspondingly decreases the volume of the flexible pharmaceutical agent compartment 104, as the osmotic engine 102 is constrained in its expansion by the rigid pump housing 101. As the flexible pharmaceutical agent compartment 104 decreases in volume, it infuses pharmaceutical agent 114 out of an opening 126 defined in the distal end of the flexible compartment 104 and into the catheter 106. According to the present invention, the flexible pharmaceutical agent compartment 104 may include and/or be made of a substantially impermeable material and may include polyethylene, PET, PETG, PETE, PE, Nylon, Urethane and/or co-polymers for example, and may be laminated with or otherwise include a layer of gold, silver and/or aluminum (to minimize permeability to gas and liquids) sputtered or otherwise deposited or incorporated therein.

Figure 3:
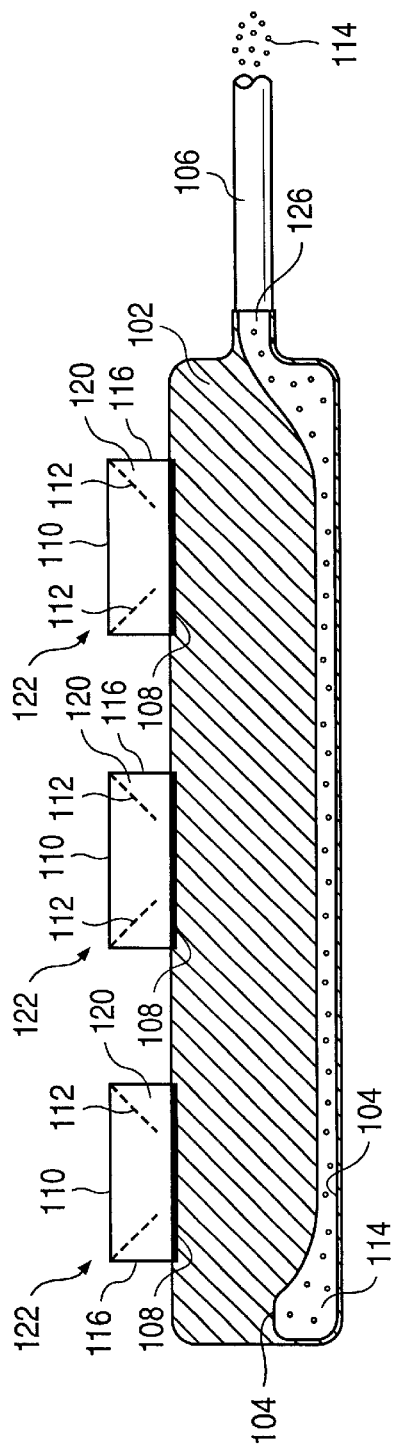
FIG. 3 shows another side cross-sectional view of the implantable osmotic pump of FIG. 1, showing the flexible pharmaceutical agent compartment in a partially emptied state.

FIG. 3 illustrates the osmotic pump system 100 of FIG. 1, in a state wherein the osmotic engine 102 has been at least partially hydrated and has increased in volume and wherein the flexible pharmaceutical agent compartment 104 has correspondingly decreased in volume, thereby infusing a volume of pharmaceutical agent 114 from the distal opening 126 of the flexible compartment 104 into the catheter 106. The hydration of the osmotic engine 102 is controlled by the surface area, composition and thickness of the semipermeable membrane(s) 108 or the sum of the contributions of the surface area, the composition and the thickness of the semipermeable membrane(s) 108. The osmotic engine is hygroscopic and may include a salt block or a "salt wafer" and/or may include an absorbent polymer, such as poly (acrylic acid), potassium salt; poly(acrylic acid), sodium salt; poly(acrylic acid-co-acrylamide), potassium salt; poly (acrylic acid), sodium salt-graft-poly(ethylene oxide); poly (2-hydroxethyl methacrylate) and/or poly(2-hydroxypropyl methacrylate) and poly(isobutylene-co-maleic acid). Suitable absorbent polymers are available from Aldrich, Inc. of Milwaukee, Wis., for example.

To assemble implantable osmotic pump system 100 according to the present invention, a blow molded flexible pharmaceutical agent compartment 104 may be inserted into the pump housing 101 and bonded (using either an adhesive or a solvent bonding technique) to the proximal end of the catheter 106. Alternatively, the pump housing 101 may include a first portion (a top portion, for example) and a second portion (a bottom portion, for example) defined with respect to selected axis of the pump housing 101, for example) that are joined and bonded together to enclose the flexible pharmaceutical agent compartment 104. The compartment 104 and catheter 106 assembly may then be bonded (adhesively, for example) to the distal opening of the pump housing 101. In this manner, the internal lumen of the catheter 106 and the opening 126 in the flexible pharmaceutical agent compartment 104 together define a fluid path for the pharmaceutical agent 114. According to an embodiment of the present invention, the flexible pharmaceutical agent compartment 104 may be free floating inside the pump housing 101 and may be attached only to the proximal end of the catheter 106 and/or to the distal opening of the pump housing 101.

Figure 5A:
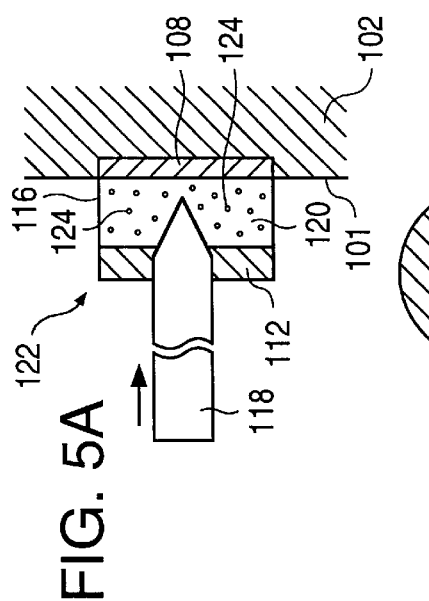
FIG. 5a shows a side view of a membrane assembly, as a lancet breaches the impermeable membrane thereof.
Figure 5B:
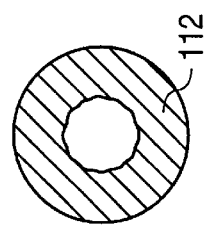
FIG. 5b shows a top view of the membrane assembly of FIG. 5a, after a lancet has breached the impermeable membrane thereof.
Figure 4A:
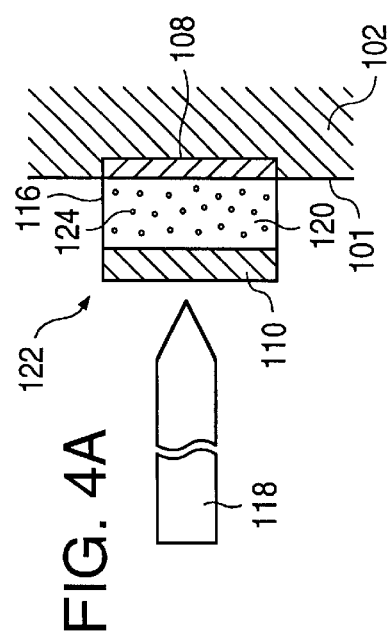
FIG. 4a shows a side view of a membrane assembly, wherein the impermeable membrane thereof is intact.
Figure 4B:
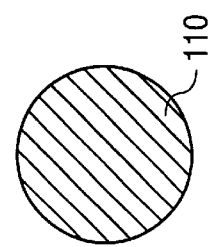

FIG. 4a shows a lancet 118 suitable for breaching the impermeable membrane 110 of the membrane assembly 122. Also shown in FIG. 4a is a side cross-sectional view of a membrane assembly 122, with an intact impermeable membrane 110, a fluoroscopic top view of which is shown in FIG. 4b. When the physician decides to initiate or increase the hydration of the osmotic engine 102, the surgeon may locate one or more of the membrane assemblies 122 by fluoroscopy and may insert a lancet 118 through the patient's skin to the implant site to breach one or more of the impermeable membranes 110, as shown in FIG. 5a. A fluoroscopic top view of a breached impermeable membrane 112 is shown at FIG. 5b and in FIG. 1, also at reference numeral 112. Once the impermeable membrane is breached, the saturated saline solution 124 in the fluid tight compartment 120 is gradually replaced with fluid from the patient and the osmotic equipotential maintained prior to the breach of the impermeable membrane 110 is lost. The osmotic pressure differential across the now exposed semipermeable membrane 108 increases, causing water from the patient to cross the semipermeable membrane 108 into the osmotic engine 102.

According to the present invention, the implantable osmotic pump system 100 does not include a movable piston. Therefore, the problems conventionally associated with piston-type osmotic pumps are not a factor in the osmotic pump system according to the present invention. The design of the pump system 100 is simplified, resulting in a less costly manufacturing process. However, the absence of movable piston in the osmotic pump system 100 according to the present invention brings about a comparatively greater advantage: the shape of the pump housing 101 need no longer be right cylindrical, as conventional implantable osmotic pumps must be. Indeed, the shape of the osmotic pump system 100 according to the present invention may now be made to conform to the topology of the implant site, resulting in a more unobtrusive and more comfortable implantable pump. The shape of the present osmotic pump housing 101 may be varied according to the shape of the cavity or environment in which it is to be implanted.

The membrane assemblies 122 may be fitted with an integrated lancet mechanism, as disclosed in the above listed co-pending and commonly-assigned US patent application entitled "Osmotic Pump Drug Delivery Systems And Methods". Moreover, the pump system 100 may be pre-loaded with one or more pharmaceutical agents, as also disclosed in the patent application referenced immediately above. For example, if the osmotic pump systems disclosed herein are intended for pain therapy, the pharmaceutical agent may include morphine-like agonists, partial agonists and mixed agonists and mixed agonists-antagonists; including but not limited to:

a) Morphine,
b) Hydromorphone,
c) Levorphanol,
d) Methadone,
e) Fentanyl,
f) Sufentanil,
g) Buprenorphine,
h) Pentazocine,
i) Butorphanol, and may further include an alpha 2-adrenoreceptor agonist, such as Clonidine or derivatives thereof.

Also, the dose of pharmaceutical agent infused within the patient may be controlled by selecting the number of impermeable membranes 110 that are breached (thereby controlling the hydration level of the osmotic engine 102), as well as by controlling the thickness, surface area and/or the composition of the semipermeable membranes 108, as also disclosed in the above-referenced patent application.

While the foregoing detailed description has described preferred embodiments of the present invention, it is to be understood that the above description is illustrative only and not limiting of the disclosed invention. Those of skill in this art will recognize other alternative embodiments and all such embodiments are deemed to fall within the scope of the present invention. Thus, the present invention should be limited only by the claims as set forth below.

What is claimed is:

1. An implantable osmotic pump system, comprising:
   a rigid pump housing defining an opening;
   a plurality of membrane assemblies fined to the pump housing, at least one of the plurality of membrane assemblies including a semipermeable membrane and an impermeable membrane initially sealing the semipermeable membrane;
   an osmotic engine within the rigid pump housing, and
   a flexible pharmaceutical agent compartment disposed within the rigid pump housing, the flexible pharmaceutical agent compartment being in fluid communication with the opening.

2. The pump system of claim 1, wherein each of the plurality of membrane assemblies includes a semipermeable membrane.

3. The pump system of claim 1, wherein the impermeable membrane is disposed away from the semipermeable membrane to define a fluid tight compartment therewith.

4. The pump system of claim 3, wherein the fluid tight compartment encloses a volume of saturated saline solution.

5. The pump system of claim 1, wherein the impermeable membrane includes a biologically inert material that is impermeable to water.

6. The pump system of claim 5, wherein the biologically inert material is radiopaque.

7. The pump system of claim 1, wherein the impermeable membrane includes at least one of titanium and stainless steel, polyethylene, polyethylene teraphthalate (PET), PETG and/or PETE.

8. The pump system of claim 1, wherein the impermeable membrane includes a layer of one of gold, silver, platinum and platinum-iridium.

9. The pump system of claim 1, wherein the osmotic engine is a hygroscopic salt.

10. The pump system of claim 1, wherein the osmotic engine includes an absorbent polymer.

11. The pump system of claim 10, wherein the absorbent polymer includes a material selected from a group including poly(acrylic acid), potassium salt; poly(acrylic acid), sodium salt; poly(acrylic acid-co-acrylamide), potassium salt; poly(acrylic acid), sodium salt-graft-poly(ethylene oxide); poly(2-hydroxethyl methacrylate); poly(2-hydroxypropyl methacrylate) and poly(isobutylene-co-maleic acid) or derivatives thereof.

12. The pump system of claim 1, wherein the pharmaceutical agent is therapeutically effective for at least one therapy selected from pain therapy, hormone therapy, gene therapy, angiogenic therapy, anti-tumor therapy and chemotherapy.

13. The pump system of claim 1, wherein the pharmaceutical agent includes an opioid.

14. The pump system of claim 1, wherein the pharmaceutical agent includes at least one of an agonist, a partial agonist, an agonist-antagonist and an alpha 2-adrenoreceptor agonist.

15. The pump system of claim 1, wherein the pharmaceutical agent includes at least one drug selected from a group including morphine, hydromorphone, levorphanol, methadone, fentanyl, suientanil, buprenorphine, pentazocine and butoxphanol.

16. The pump system of claim 1, wherein the flexible pharmaceutical agent compartment includes at least one of polyethylene, polyethylene teraphthalate (PET), PETG, PETE, nylon, urethane and co-polymers.

17. The pump system of claim 16, wherein the pharmaceutical agent compartment includes a metallic layer.

18. The pump system of claim 17, wherein the metallic layer includes at least one of aluminum, platinum, gold and silver.

19. The pump system of claim 1, further comprising a catheter attached to the opening and to a corresponding opening in the flexible pharmaceutical agent compartment so as to define a fluid path from the flexible pharmaceutical agent compartment through the opening of the pump housing to the catheter.

20. The pump system of claim 19, wherein the flexible pharmaceutical agent compartment is free floating inside the pump housing and is attached only to at least one of the catheter and the opening of the pump housing.

21. The pump system of claim 1, wherein the pump housing has a non-cylindrical shape.

22. The pump system of claim 1, wherein the pump housing has a shape that conforms to a patient anatomy at an implantation site.

23. The pump system of claim 1, wherein the pump housing includes a proximal end, a distal end and a sidewall, and wherein the at least one membrane assembly is fitted to the sidewall.

24. The pump system of claim 1, wherein the at least one membrane assembly includes an array of membrane assemblies, each of which includes a semipermeable membrane initially sealed by a radiopaque impermeable membrane adapted to be breached with a lancet.

25. An implantable osmotic pump, comprising:
   a pump housing;
   an osmotic engines, the osmotic engine being disposed within the pump housing;
   a plurality of semipermeable membranes, each of the plurality of semipermeable membranes being configured to allow water to cross from a patient into the pump housing to the osmotic engine, and
   a flexible pharmaceutical agent compartment adapted to enclose a volume of pharmaceutical agent.

26. The osmotic pump of claim 25, wherein the flexible pharmaceutical agent compartment is adapted to infuse the volume of pharmaceutical agent at a selected infusion rate as the osmotic engine hydrates and swells with the water from the patient, the selected infusion rate being related to at least one of a thickness, a composition and a surface area of the semipermeable membrane.

27. The osmotic pump of claim 25, wherein the pump housing includes a proximal end, a distal end and a sidewall, the semipermeable membrane being fitted to the sidewall.

28. The osmotic pump of claim 25, wherein the pump housing includes a proximal end, a distal end and a sidewall, the semipermeable membrane being fitted to the proximal end.

29. The osmotic pump of claim 25, wherein each of the plurality of semipermeable membranes is fitted with an impermeable membrane that initially seals the semipermeable membrane.

30. The osmotic pump of claim 29, wherein the impermeable membrane is radiopaque.

31. The osmotic pump of claim 25, wherein the osmotic engine is at least co-extensive with the flexible pharmaceutical agent compartment.

32. The osmotic pump of claim 25, wherein the pump housing is cylindrical.

33. The osmotic pump of claim 32, wherein the pump housing has a height and a diameter and wherein the height of the pump housing is no greater than the diameter of the pump housing.

34. The osmotic pump of claim 25, wherein the pump housing has a non-cylindrical shape.

35. The osmotic pump of claim 25, wherein the phamaceutical agent is therapeutically effective for at least one therapy selected from pain therapy, hormone therapy, gene therapy, angiogenic therapy, anti-tumor therapy and chemotherapy.

36. The osmotic pump of claim 25, wherein the pharmaceutical agent includes an opioid.

37. The osmotic pump of claim 25, wherein the pharmaceutical agent includes at least one of an agonist, a partial agonist, an agonist-antagonist and an alpha 2-adrenoreceptor agonist.

38. The osmotic pump of claim 25, wherein the pharmaceutical agent includes at least one drug selected from a group including morphine, hydromorphone, levorphanol, methadone, fentanyl, sufentanil, buprenorphine, pentazocine and butorphanol.

39. An implantable osmotic pump system, comprising:
   a rigid pump housing defining an opening;
   at least one membrane assembly fitted to the pump housing, the membrane assembly including a semipermeable membrane and an impermeable membrane initially sealing the semipermeable membrane and adapted to be breached by a lancet, the impermeable membrane being disposed away from the semipermeable membrane to define a fluid tight compartment, the fluid tight compartment enclosing a volume of an aqueous solution;
   an osmotic engine within the rigid pump housing, and
   a flexible pharmaceutical agent compartment disposed within the rigid pump housing, the flexible pharmaceutical agent compartment being in fluid communication with the opening.

40. The pump system of claim 39, wherein the aqueous solution includes a saturated saline solution.

41. An implantable osmotic pump system, comprising:
   a rigid pump housing defining an opening;
   at least one membrane assembly fitted to the pump housing, the membrane assembly including a semipermeable membrane and an impermeable membrane initially sealing the semipermeable membrane and adapted to be breached by a lancet, the impermeable membrane including a layer of one of gold, silver, platinum and platinum-iridium;
   an osmotic engine within the rigid pump housing, and
   a flexible pharmaceutical agent compartment disposed within the rigid pump housing, the flexible pharmaceutical agent compartment being in fluid communication with the opening.

42. An implantable osmotic pump system, comprising:
a rigid pump housing defining an opening;
a plurality of membrane assemblies fitted to the pump housing;
an osmotic engine within the rigid pump housing, and
a flexible pharmaceutical agent compartment disposed within the rigid pump housing, the flexible pharmaceutical agent compartment being in fluid communication with the opening.

43. The osmotic pump system of claim 42, wherein at least one of the plurality of membrane assemblies includes a semipermeable membrane that is fined with an impermeable membrane that initially seals the semipermeable membrane.

44. The osmotic pump system of claim 43, wherein the impermeable membrane being disposed away from the semipermeable membrane to define a fluid tight compartment, the fluid tight compartment enclosing a volume of an aqueous solution.

45. The osmotic pump system of claim 44, the aqueous solution includes a saturated saline solution.

* * * * *

UNITED STATES PATENT AND TRADEMARK OFFICE
CERTIFICATE OF CORRECTION

PATENT NO.      : 6,464,688 B1
DATED           : October 15, 2002
INVENTOR(S)     : Harper et al.

It is certified that error appears in the above-identified patent and that said Letters Patent is hereby corrected as shown below:

Column 8,
Line 3, please delete "fined" and insert -- fitted --.

Column 9,
Line 3, please delete "engines" and insert -- engine --.

Column 12,
Line 3, please delete "fined" and insert -- fitted --.

Signed and Sealed this

Fourth Day of March, 2003

JAMES E. ROGAN
*Director of the United States Patent and Trademark Office*